US006712784B2

(12) United States Patent
Huang

(10) Patent No.: US 6,712,784 B2
(45) Date of Patent: Mar. 30, 2004

(54) DRUG DELIVERY DEVICE WITH A FLEXIBLE GRATING TO HINDER UNFORCED REMOVAL OF A DRUG IN SOLID FORM FROM AN INSERT TUBE

(76) Inventor: Deborah Huang, 7F, No. 5, Sec. 3, Liu-Chuan E. Rd., Chung Dist., Taichung City (TW)

( * ) Notice: Subject to any disclaimer, the term of this patent is extended or adjusted under 35 U.S.C. 154(b) by 0 days.

(21) Appl. No.: 10/078,157

(22) Filed: Feb. 20, 2002

(65) Prior Publication Data

US 2003/0158510 A1 Aug. 21, 2003

(51) Int. Cl.[7] .................. A61M 31/00; A61M 5/00; A61F 13/20; A61K 9/02
(52) U.S. Cl. .................. 604/60; 604/236; 604/11; 604/288; 604/187
(58) Field of Search .................. 604/515, 59, 60–65, 604/15, 110, 236, 288, 282, 11

(56) References Cited

U.S. PATENT DOCUMENTS

| | | | |
|---|---|---|---|
| 2,754,822 A | 7/1956 | Emelock | 128/264 |
| 3,347,234 A | 10/1967 | Voss | 128/260 |
| 3,667,465 A | 6/1972 | Voss | 128/271 |
| 4,318,405 A | * | 3/1982 | Sneider | 604/15 |
| 4,636,202 A | * | 1/1987 | Lowin et al. | 604/236 |
| 5,085,640 A | * | 2/1992 | Gibbs | 604/110 |
| 6,364,854 B1 | * | 4/2002 | Ferrer et al. | 604/60 |

FOREIGN PATENT DOCUMENTS

EP 0 252214 A1 1/1988

* cited by examiner

Primary Examiner—Brian L. Casler
Assistant Examiner—Roz Maiorino
(74) Attorney, Agent, or Firm—Morgan Lewis & Bockius LLP

(57) ABSTRACT

A drug delivery device includes an insert tube and an elongate plunger. The insert tube has a tubular wall that confines a passage and that has drug entrance and release ends. The drug release end has first and second radial parts, and is provided with a flexible grating that includes sets of first and second flexible strips. The first and second flexible strips extend from the first and second radial parts of the drug release end, respectively. The elongate plunger has a drug pushing end and an operating end, is slidably movable in the passage, and has a length sufficient to enable the drug pushing end to push a drug in the passage to move out of the passage and spread apart the first and second flexible strips for delivering the drug into a body cavity.

11 Claims, 8 Drawing Sheets

DRUG DELIVERY DEVICE WITH A FLEXIBLE GRATING TO HINDER UNFORCED REMOVAL OF A DRUG IN SOLID FORM FROM AN INSERT TUBE

BACKGROUND OF THE INVENTION

1. Field of the Invention

The invention relates to a drug delivery device, more particularly to a drug delivery device that dispenses with the need to insert a finger into a body cavity during the delivery process.

2. Description of the Related Art

Suppositories are usually used for treating vaginal infections or diseases in the anus. Mainly, the suppository is inserted into the vagina or anus. Referring to FIG. 1, a conventional way of delivering a drug 10 into a body cavity is done by aiming one end 11 of the drug 10 at the opening of the vagina or anus, after which a finger is used to push the drug 10 deep into the vagina or anus. However, this conventional way of delivering the drug 10 into the body cavity has the following disadvantages:

1. It is necessary to wash the hands thoroughly or to use sterilized hand gloves during the drug delivery process.
2. The inner wall of the vagina or anus is easily scratched and injured by the fingernail on the inserted finger, thereby resulting in pain.
3. The drug delivery process may induce emotional trauma.
4. Because the drug cannot be delivered to a proper depth and position due to the limited finger length, the effect of the drug is reduced, thereby prolonging the course of treatment.

SUMMARY OF THE INVENTION

Therefore, the main object of the present invention is to provide a drug delivery device that dispenses with the need to insert a finger into a body cavity during the delivery process and that is simple to use.

Accordingly, a drug delivery device of this invention comprises an insert tube and an elongate plunger. The insert tube has a tubular wall that confines a passage extending in an axial direction for receiving a drug in solid form. The tubular wall has a drug entrance end adapted for admitting the drug into the passage, and a drug release end opposite to the drug entrance end in the axial direction and adapted to be inserted into a body cavity. The drug release end has opposite first and second radial parts. The insert tube is provided with a flexible grating at the drug release end so as to hinder unforced removal of the drug from the passage via the drug release end. The flexible grating includes a set of first flexible strips that extend from the first radial part toward the second radial part, and a set of second flexible strips that extend from the second radial part toward the first radial part. The elongate plunger has a drug pushing end and an operating end opposite to the drug pushing end in the axial direction. The plunger is slidably extended into the passage via the drug entrance end of the tubular wall such that the drug pushing end is disposed proximate to the drug release end of the tubular wall, and such that the operating end is disposed outwardly of the passage and is adjacent to the drug entrance end of the tubular wall. The plunger is movable in the passage, and has a length sufficient to enable the drug pushing end to push the drug to move out of the passage at the drug release end and spread apart the first and second flexible strips of the flexible grating for delivering the drug into the body cavity.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENTS

Figure 1:
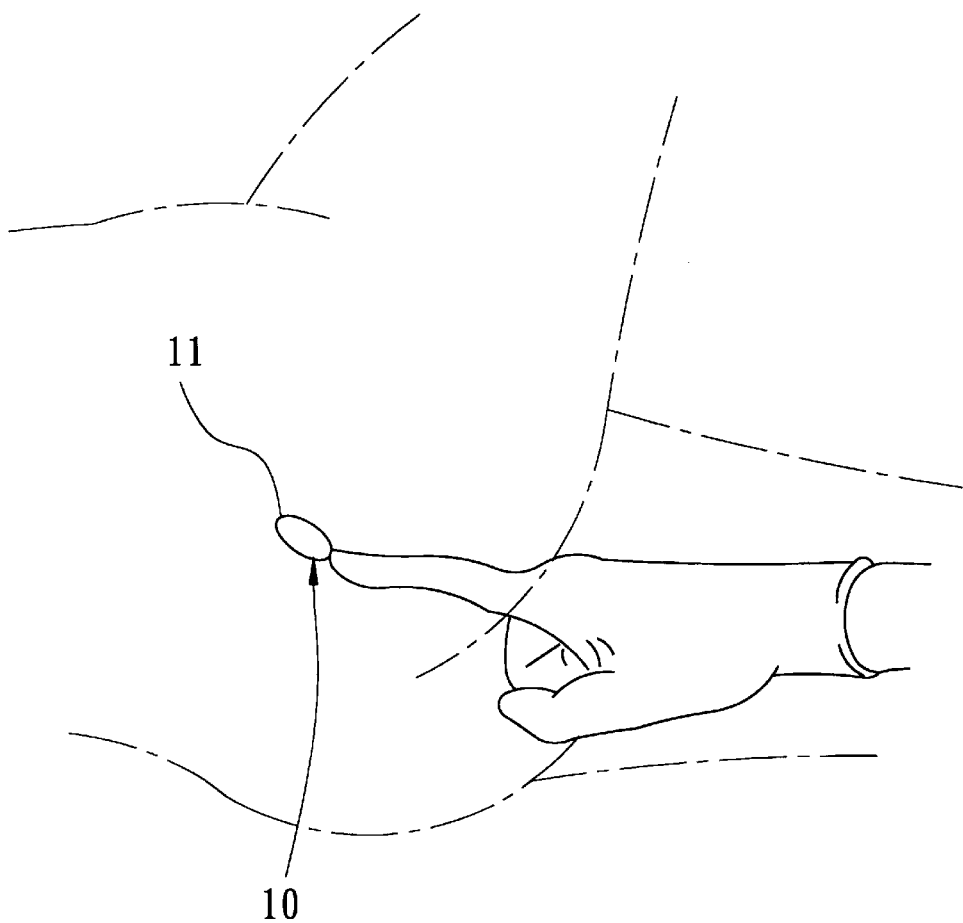
FIG. 1 illustrates a conventional way of delivering a drug into a body cavity.
Figure 2:
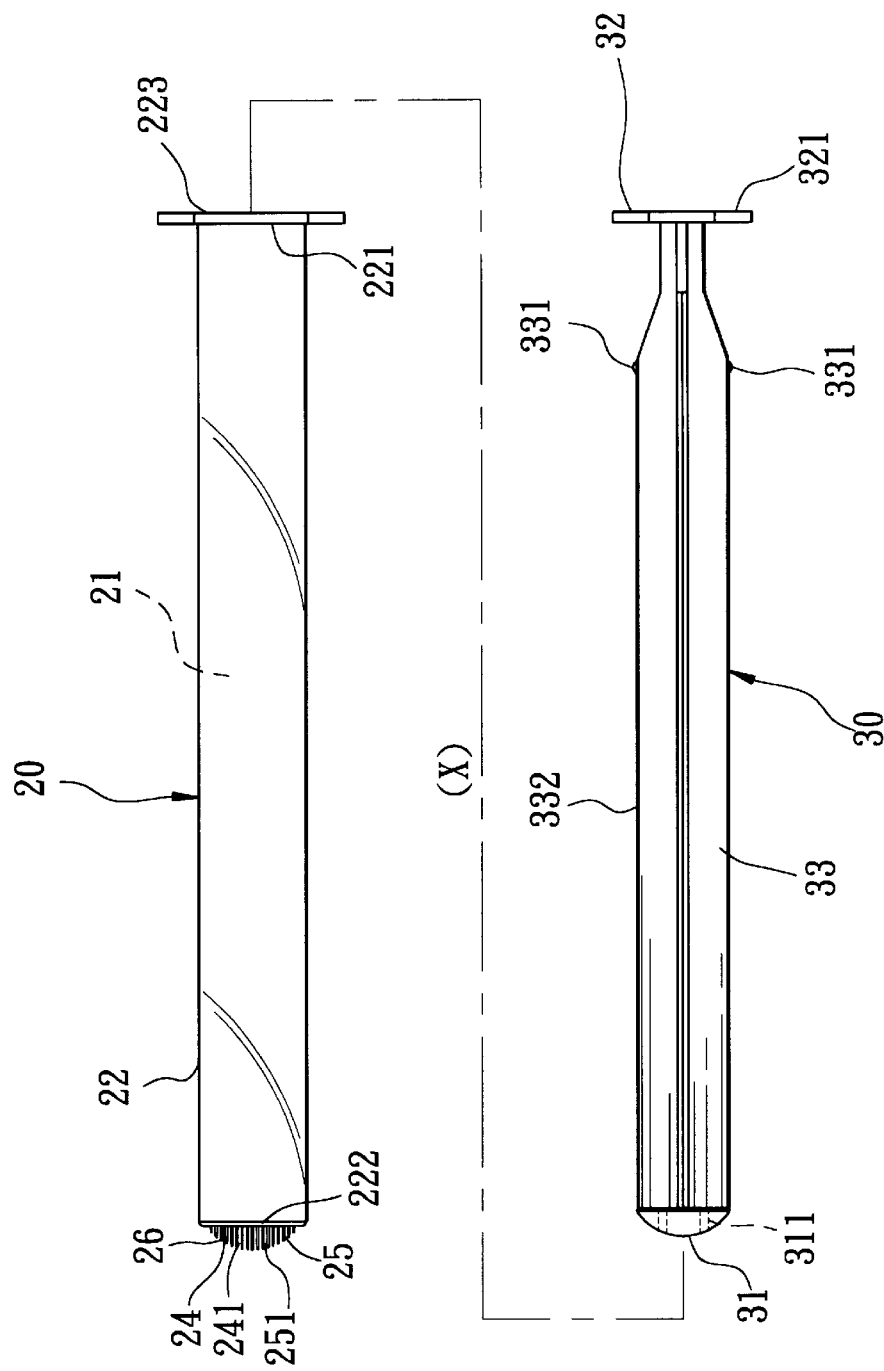
FIG. 2 is an exploded schematic view of the preferred embodiment of a drug delivery device according to the present invention.
Figure 3:
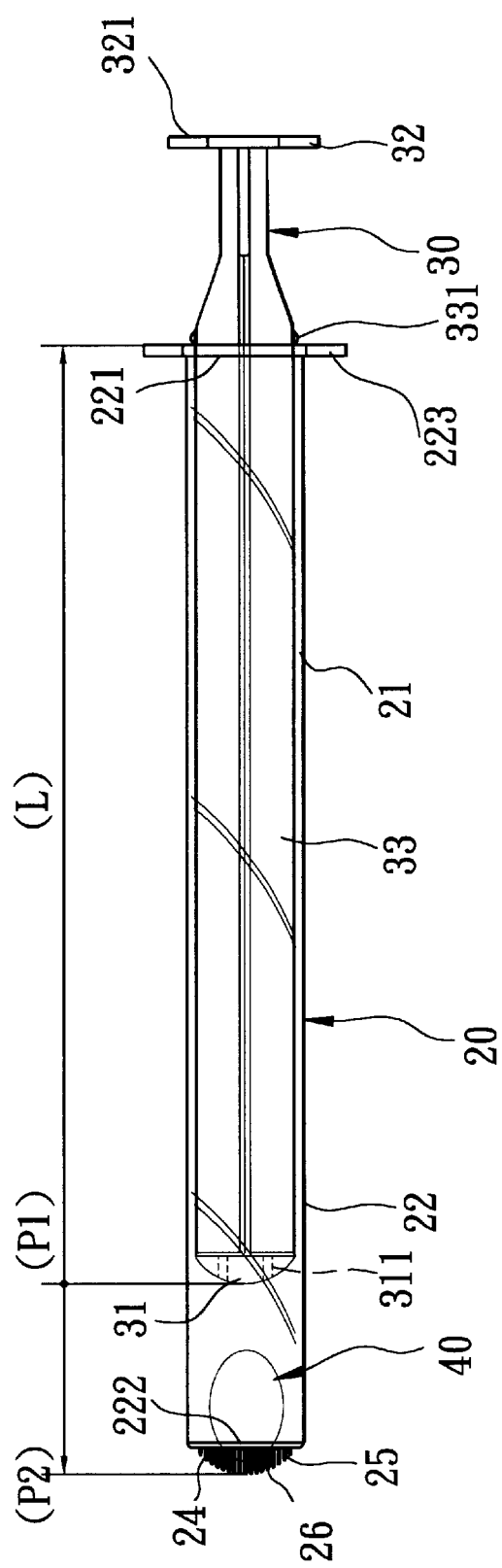
FIG. 3 is an assembled schematic view of the preferred embodiment.
Figure 4:
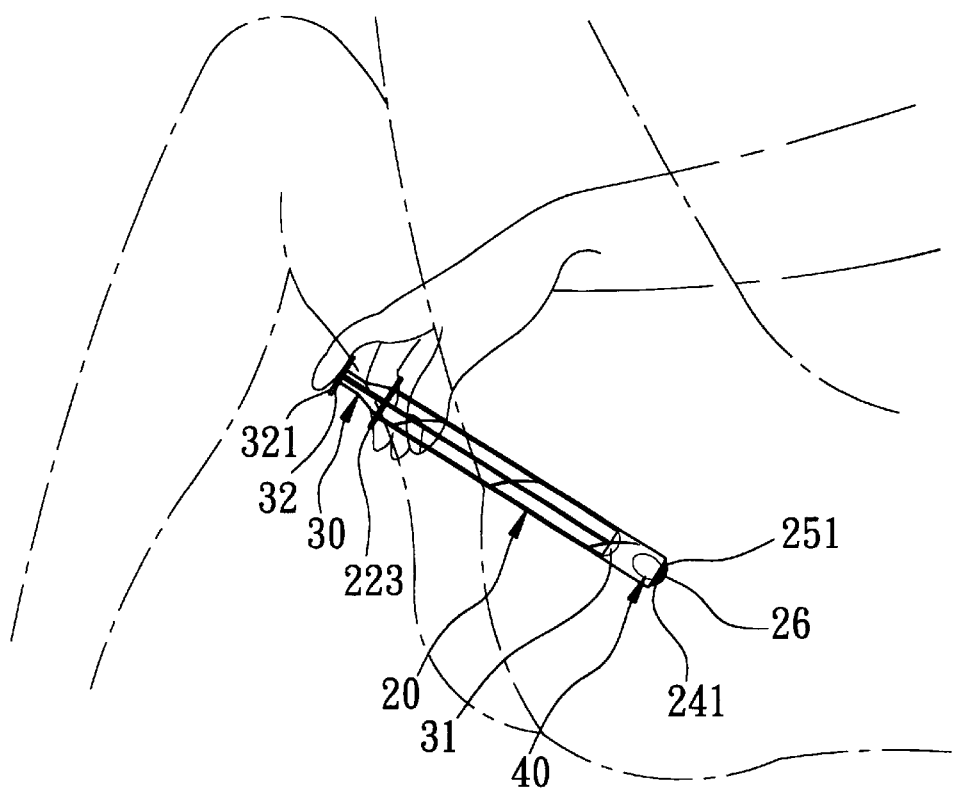
FIG. 4 illustrates the preferred embodiment in a state of delivering a drug into a body cavity.
Figure 5:
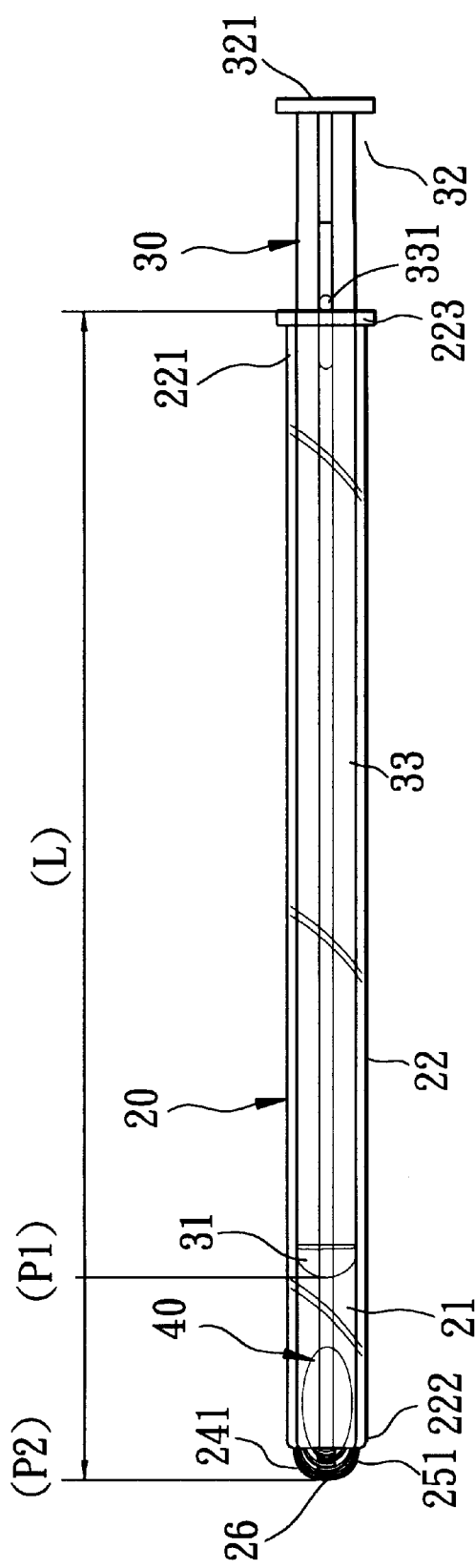
FIG. 5 illustrates how the drug is hindered by a flexible grating at a drug release end of an insert tube of the preferred embodiment.
Figure 6:
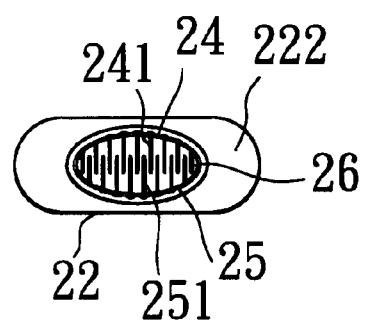
FIG. 6 is a schematic end view of the insert tube to illustrate the flexible grating.
Figure 7:
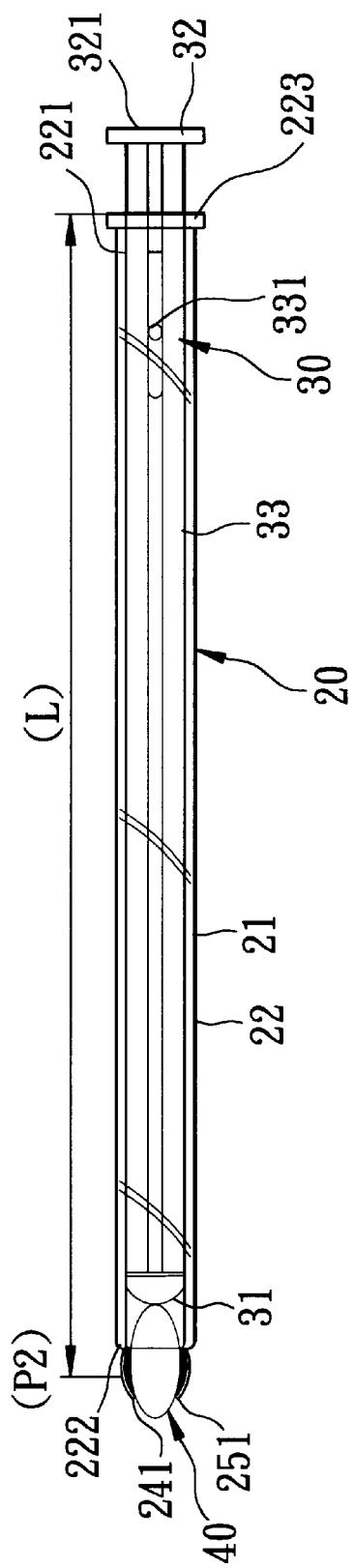
FIG. 7 illustrates how the drug is pushed out of the insert tube by a plunger of the preferred embodiment.

Referring to FIGS. 2 to 8, the preferred embodiment of a drug delivery device according to the present invention is shown to comprise an insert tube 20 and an elongate plunger 30. The insert tube 20 has a tubular wall 22 that confines a passage 21 extending in an axial direction (X) for receiving a drug 40 in solid form. The tubular wall 22 can be shaped as a circular or oval cylinder, and has a drug entrance end 221 and a drug release end 222. The drug entrance end 221 is adapted for admitting the drug 40 into the passage 21, and is formed with a first radial outward flange 223. The drug release end 222 is opposite to the drug entrance end 221 at a distance (L) in the axial direction (X), and is adapted to be inserted into a body cavity. The drug release end 222 has opposite first and second radial parts 24, 25, and is provided with a flexible grating 26 so as to hinder unforced removal of the drug 40 from the passage 21 via the drug release end 222, as best shown in FIG. 3. The flexible grating 26 is made of a flexible material, and includes a set of first flexible curved strips 241 and a set of second flexible curved strips 251 (see FIGS. 2 and 3). The first flexible curved strips 241 extend from the first radial part 24 toward the second radial part 25. The second flexible curved strips 251 extend from the second radial part 25 toward the first radial part 24.

Figure 8:
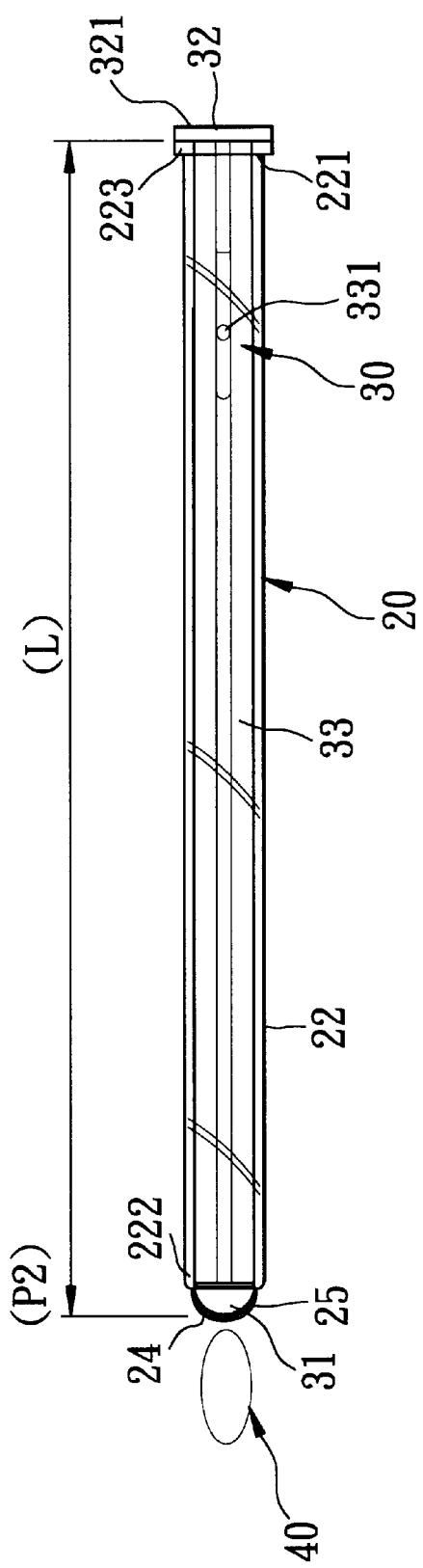
FIG. 8 illustrates how a radial outward flange of the plunger is prevented from extending into the insert tube.

The elongate plunger 30 has a drug pushing end 31 and an operating end 32 opposite to the drug pushing end 31 in the axial direction (X), and an intermediate plunger part 33 between the drug pushing end 31 and the operating end 32. The drug pushing end 31 is formed with a plurality of vent holes 311 that extend in the axial direction (X), and has a convex pushing surface. The curved strips 241, 251 complement the pushing surface of the drug pushing end 31. The drug pushing end 31 further has a diameter smaller than that of the passage 21 in the insert tube 20. The operating end 32 is formed with a second radial outward flange 321 that abuts against the first radial outward flange 223 to prevent the operating end 32 of the plunger 30 from extending into the passage 21, as best shown in FIG. 8. The intermediate plunger part 33 includes four axially extending and angularly spaced apart radial wing plates 332 that are in sliding contact with the tubular wall 22. Each of two opposite wing plates 332 is formed with a radial friction rib 331 adjacent to the operating end 32 to increase friction between the plunger 30 and the insert tube 20 when the plunger 30 is disposed at a preparation position (P1) relative to the drug release end 222 of the tubular wall 22 in preparation for delivering the drug 40 into the body cavity (see FIG. 3). The drug 40 is confined in the passage 21 at a space bounded by the preparation position (P1) and a release position (P2) of the plunger 30.

The plunger 30 is slidably extended into the passage 21 via the drug entrance end 221 of the tubular wall 22 such that the drug pushing end 31 is disposed proximate to the drug release end 222 of the tubular wall 22, and such that the operating end 32 is disposed outwardly of the passage 21 and is adjacent to the drug entrance end 212 of the tubular wall 22. The plunger 30 is movable in the passage 21 in the axial direction (X), and has a length sufficient to enable the drug pushing end 31 to push the drug 40 to move out of the passage 21 at the drug release end 222 and spread apart the first and second flexible strips 241, 251 of the flexible grating 26 for delivering the drug 40 into the body cavity.

During use, after the drug 40 is disposed in the passage 21 via the drug entrance end 212 of the insert tube 20, the plunger 30 is inserted into the insert tube 20 such that the wing plates 33 are in sliding contact with the tubular wall 22. The drug 40 is pushed by the plunger 30 to the space between the preparation position (P1) and the release position (P2), and is confined therebetween. At this time, the friction ribs 331 of the wing plates 332 abut against the drug entrance end 221 of the tubular wall 22.

Referring back to FIG. 4, the insert tube 20 is then inserted into a proper depth of the vagina or anus. The friction ribs 331 come into contact with the tubular wall 22 as the operating end 32 of the plunger 30 is pushed. The plunger 30 is pushed continuously until the second radial outward flange 321 abuts against the first radial outward flange 223, and the drug pushing end 31 of the plunger 30 reaches the drug release end 222 of the insert tube 20, thereby pushing the drug 40 to move out of the flexible grating 26 at the drug release end 222 and into the body cavity. Thus, the drug is conveniently delivered into a proper depth and position of the body cavity.

It should be noted that, when the drug delivery device of the present invention is in use, the hands need not come into contact with the drug 40 during the actual delivery process so that sanitation can be maintained. Furthermore, the drug delivery device of the present invention is simple and easy to operate. Moreover, injury to the body cavity can be minimized due to the cylindrical shape of the insert tube 20 and the flexibility of the flexible grating 26, thereby enhancing comfort during use.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. A drug delivery device comprising:
   an insert tube having a tubular wall that confines a passage extending in an axial direction for receiving a drug in solid form, said tubular wall having a drug entrance end adapted for admitting the drug into said passage, and a drug release end opposite to said drug entrance end in the axial direction and adapted to be inserted into a body cavity, said drug release end having opposite first and second radial parts, said insert tube being provided with a flexible grating at said drug release end to hinder unforced removal of the drug from said passage via said drug release end, said flexible grating including a set of first flexible strips that extend from said first radial part toward said second radial part, and a set of second flexible strips that extend from said second radial part toward said first radial part;
   an elongate plunger having a drug pushing end and an operating end opposite to said drug pushing end in the axial direction, said plunger being slidably extended into said passage via said drug entrance end of said tubular wall such that said drug pushing end is disposed proximate to said drug release end of said tubular wall, and such that said operating end is disposed outwardly of said passage and is adjacent to said drug entrance end of said tubular wall, said plunger being movable in said passage and having a length sufficient to enable said drug pushing end to push the drug to move out of said passage at said drug release end and spread apart said first and second flexible strips of said flexible grating for delivering the drug into the body cavity,
   wherein said drug entrance end of said tubular wall is formed with a first radial outward flange, and
   wherein said operating end of said plunger is formed with a second radial outward flange that abuts against said first radial outward flange to prevent said operating end of said plunger from extending into said passage.

2. A drug delivery device comprising:
   an insert tube having a tubular wall that confines a passage extending in an axial direction for receiving a drug in solid form, said tubular wall having a drug entrance end adapted for admitting the drug into said passage, and a drug release end opposite to said drug entrance end in the axial direction and adapted to be inserted into a body cavity, said drug release end having opposite first and second radial parts, said insert tube being provided with a flexible grating at said drug release end to hinder unforced removal of the drug from said passage via said drug release end, said flexible grating including a set of first flexible strips that extend from said first radial part toward said second radial part, and a set of second flexible strips that extend from said second radial part toward said first radial part; and
   an elongate plunger having a drug pushing end and an operating end opposite to said drug pushing end in the axial direction, said plunger being slidably extended into said passage via said drug entrance end of said tubular wall such that said drug pushing end is disposed proximate to said drug release end of said tubular wall, and such that said operating end is disposed outwardly of said passage and is adjacent to said drug entrance end of said tubular wall, said plunger being movable in said passage and having a length sufficient to enable said drug pushing end to push the drug to move out of said passage at said drug release end and spread apart said first and second flexible strips of said flexible grating for delivering the drug into the body cavity;
   wherein said plunger further has an intermediate plunger part between said drug pushing end and said operating end, said intermediate plunger part including a plurality of axially extending and angularly spaced apart radial wing plates that are in sliding contact with said tubular wall.

3. The drug delivery device as claimed in claim 2, wherein said intermediate plunger part is formed with a radial friction rib adjacent to said operating end to increase friction between said plunger and said insert tube when said plunger is disposed at a preparation position relative to said drug release end of said tubular wall in preparation for delivering the drug into the body cavity.

4. The drug delivery device as claimed in claim 2, wherein said drug pushing end of said plunger is formed with a plurality of vent holes that extend in the axial direction.

5. A drug delivery device comprising:

an insert tube having a tubular wall that confines a passage extending in an axial direction for receiving a drug in solid form, said tubular wall having a drug entrance end adapted for admitting the drug into said passage, and a drug release end opposite to said drug entrance end in the axial direction and adapted to be inserted into a body cavity, said drug release end having opposite first and second radial parts, said insert tube being provided with a flexible grating at said drug release end to hinder unforced removal of the drug from said passage via said drug release end, said flexible grating including a set of first flexible strips that extend from said first radial part toward said second radial part, and a set of second flexible strips that extend from said second radial part toward said first radial part; and an elongate plunger having a drug pushing end and an operating end opposite to said drug pushing end in the axial direction, said plunger being slidably extended into said passage via said drug entrance end of said tubular wall such that said drug pushing end is disposed proximate to said drug release end of said tubular wall, and such that said operating end is disposed outwardly of said passage and is adjacent to said drug entrance end of said tubular wall, said plunger being movable in said passage and having a length sufficient to enable said drug pushing end to push the drug to move out of said passage at said drug release end and spread apart said first and second flexible strips of said flexible grating for delivering the drug into the body cavity wherein said drug pushing end of said plunger has a convex pushing surface, and said first and second flexible strips are curved strips that complement said pushing surface of said drug pushing end.

6. The drug delivery device as claimed in claim 5, wherein said tubular wall of said insert tube is shaped as a circular cylinder.

7. The drug deliver device as claimed in claim 5, wherein said tubular wall of said insert tube is shaped as an oval cylinder.

8. The drug delivery device as claimed in claim 1, wherein said tubular wall of said insert tube is shaped as a circular cylinder.

9. The drug deliver device as claimed in claim 1, wherein said tubular wall of said insert tube is shaped as an oval cylinder.

10. The drug delivery device as claimed in claim 2, wherein said tubular wall of said insert tube is shaped as a circular cylinder.

11. The drug deliver device as claimed in claim 2, wherein said tubular wall of said insert tube is shaped as an oval cylinder.

* * * * *